US011540897B2

(12) United States Patent  
Snow et al.

(10) Patent No.: US 11,540,897 B2  
(45) Date of Patent: Jan. 3, 2023

(54) ANATOMICAL SIDE X-RAY MARKERS COMPRISING NON-METALLIC MATERIAL

(71) Applicant: The Provost, Fellows, Foundation Scholars, and the Other Members of Board, of the College of the Holy and Undivided Trinity of Queen Elizabeth, Near Dublin, Dublin (IE)

(72) Inventors: Aisling Snow, Dublin (IE); Fiona Snow, Dublin (IE)

(73) Assignee: THE PROVOST, FELLOWS, FOUNDATION SCHOLARS, AND THE OTHER MEMBERS OF THE BOARD, OF THE COLLEGE OF THE HOLY AND UNDIVIDED TRINITY OF QUEEN ELIZABETH, Dublin (IE)

( * ) Notice: Subject to any disclaimer, the term of this patent is extended or adjusted under 35 U.S.C. 154(b) by 212 days.

(21) Appl. No.: 16/767,975

(22) PCT Filed: Nov. 27, 2018

(86) PCT No.: PCT/EP2018/082686  
§ 371 (c)(1),  
(2) Date: May 28, 2020

(87) PCT Pub. No.: WO2019/105925  
PCT Pub. Date: Jun. 6, 2019

(65) Prior Publication Data  
US 2020/0367991 A1 Nov. 26, 2020

(30) Foreign Application Priority Data  
Nov. 28, 2017 (GB) .................... 1719736

(51) Int. Cl.  
*H05G 1/28* (2006.01)  
*A61B 90/00* (2016.01)

(52) U.S. Cl.  
CPC ...... *A61B 90/39* (2016.02); *A61B 2090/3966* (2016.02)

(58) Field of Classification Search  
CPC . A61B 90/39; A61B 2090/3966; A61B 90/37; A61B 90/96; A61B 2090/3995; A61B 2090/3983; A61B 2090/3762; A61B 2090/374; A61B 2090/3958; A61B 5/6842; A61B 6/04; A61B 6/469;  
(Continued)

(56) References Cited

U.S. PATENT DOCUMENTS 5,232,452 A * 8/1993 Russell .................. A61B 90/39  
378/163  
6,459,772 B1 * 10/2002 Wiedenhoefer ........ G01B 15/00  
378/207

(Continued)

*Primary Examiner* — Irakli Kiknadze  
(74) *Attorney, Agent, or Firm* — Brian J. Colendreo; Jeffrey T. Placker; Holland & Knight LLP

(57) ABSTRACT

A disposable x-ray side marker (100) comprises a non-metallic material (108) having a sufficiently high linear attenuation coefficient to be radiographically visible. The material (108) may be mouldable, and may be or comprise gypsum. The material (108) may have an average atomic number greater than or equal to 11, and may have a linear attenuation coefficient greater than that of mammalian soft tissue.

16 Claims, 12 Drawing Sheets

(58) Field of Classification Search
CPC . A61B 2090/3904; A61B 6/502; A61B 90/98; A61B 34/20; A61B 6/4258; A61B 6/4405; A61B 6/488; A61B 6/508; A61B 6/027; A61B 6/4417; A61B 6/025; A61B 6/461; A61B 6/12; A61B 6/50; A61B 5/4255; A61B 6/481; A61B 5/073; A61B 5/42; A61B 50/22; A61B 6/582; A61B 6/032; A61B 6/584; A61B 6/14; A61B 6/58; A61B 6/583; A61B 6/035; A61B 6/44; A61B 6/4085; A61B 6/501; A61B 6/5217; A61B 6/505; A61B 50/30; A61B 5/01; A61B 90/94; A61B 6/02; A61B 2090/3912; A61B 2090/3991; A61B 2017/00004; A61B 90/11; A61B 2034/105; A61B 2034/2072; A61B 2034/2055; A61B 2017/00716; A61B 2034/2057; A61B 5/1076; A61B 5/1072; A61B 2562/17; G03B 42/047; A61N 5/1049; A61N 2005/1061; A61N 2005/1055; A61N 1/056; A61N 1/0573; A61N 5/1075; A61N 5/1039; A61K 49/0404; A61K 49/0414; G01N 23/04; G01R 33/58; G16H 50/30; G16H 20/40; H04L 27/2273
USPC .................................................. 378/62, 163
See application file for complete search history.

(56) References Cited

U.S. PATENT DOCUMENTS

| | | | | |
|---|---|---|---|---|
| 2004/0086082 | A1* | 5/2004 | Foos | A61B 5/1072 378/163 |
| 2009/0022272 | A1* | 1/2009 | Joseph | A61B 5/6842 378/162 |
| 2013/0266124 | A1* | 10/2013 | Coursolle | A61B 90/39 378/163 |
| 2015/0329423 | A1* | 11/2015 | Fisher | C04B 28/14 106/781 |
| 2018/0103979 | A1* | 4/2018 | Arimitsu | A61B 10/0233 |

* cited by examiner

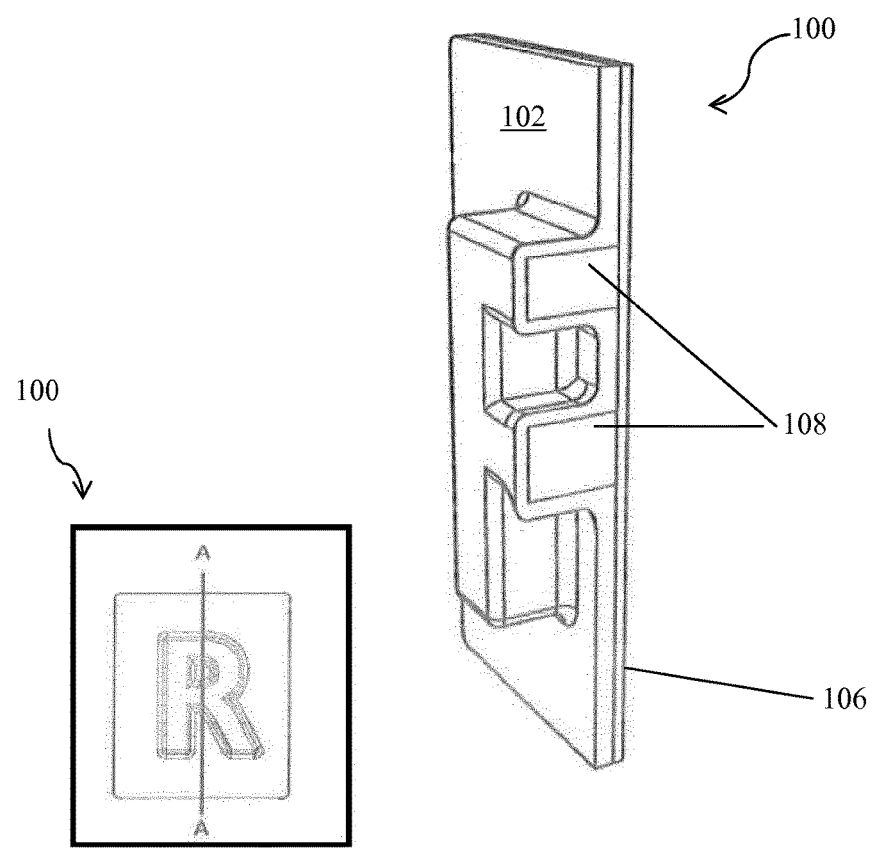
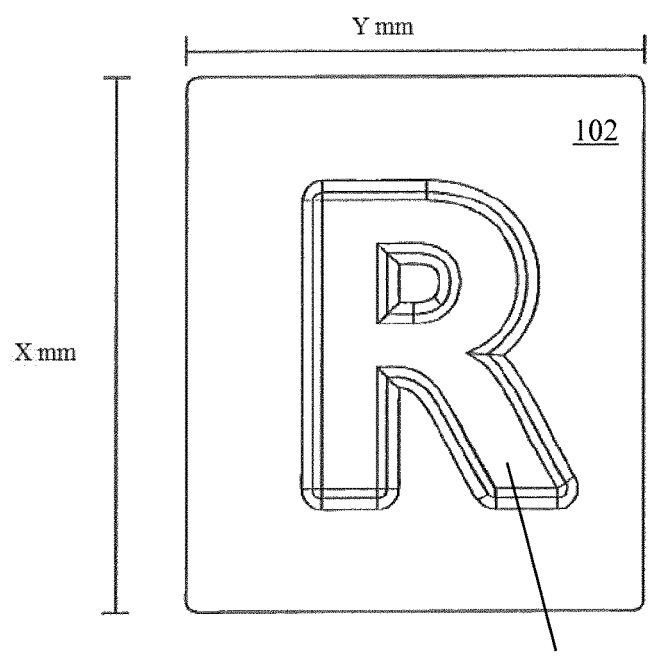
Figure 2B
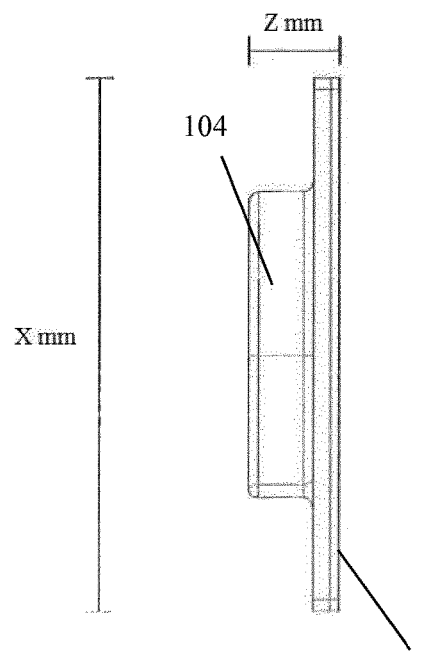
Figure 2C
Figure 2A

ANATOMICAL SIDE X-RAY MARKERS COMPRISING NON-METALLIC MATERIAL

CROSS-REFERENCE TO RELATED APPLICATIONS

This application is a U.S. National Stage of International Patent Application No. PCT/EP2018/082686, filed 27 Nov. 2018, which claims priority to Great Britain Patent Application No: 1719736.9, filed on 28 Nov. 2017, the disclosure of which is incorporated herein by reference in its entirety.

The invention relates to markers for use in taking radiographic images, i.e. images formed using x-rays, for example to label left and right sides of the image. In particular, the invention relates to disposable x-ray side markers (radiographic markers). In particular, but not exclusively, the invention relates to low-cost x-ray markers, which may also be more environmentally friendly than their current counterparts.

Radiographic images are marked to ensure that radiographic images are not mixed up, which, in particular for clinical radiographic images, could potentially lead to incorrect diagnosis and treatment. X-ray markers (also referred to as radiographic markers or side markers) used in the field comprise metal, which is sufficiently attenuating to show up clearly in a radiographic image. One or more markers are positioned on or near the subject of a radiograph and show up in the image. The markers may be shaped like an "L" or "R" to indicate left or right, and may contain additional or alternative identifying details.

The skilled person will appreciate that a side marker is required on all clinical radiographic images, and that a side marker is required to indicate either right or left sided anatomy. "L" is commonly used to indicate left and "R" is commonly used to indicate right, although the skilled person would appreciate that different, unambiguous, letters or symbols may be chosen in some circumstances, for example dependent on the language, alphabet, or syllabary in the place of use (e.g. Chinese or Japanese characters for left and right may be used).

It is common and accepted practice that side markers may be placed backwards, or in any location within the image (field of view), which is why only one of a left indicator or a right indicator can be present on a single X-ray side marker. An X-ray marker including both an "L" and an "R" could not be used as a side marker as the indication of side would not be unambiguous. A left or right indicator may also be referred to as a left or right designation, respectively.

The failure to place a marker, or the visibility of two different side designations (for example an "R" and an "L") on a single marker, in the field of view renders the image uninterpretable in a safe way. Right and left designations are permissible in a single field of view only when used separately (i.e. on separate markers) and to indicate two anatomical sides where both sides are visible in the image. Use of two different side indicators (whether or not on the same marker) on an image that includes only one anatomic side, for example one hand, would render the image uninterpretable.

In the healthcare environment, there is a need for sanitation to reduce the risk of infection or cross-contamination when taking clinical images. Current x-ray markers are therefore intended to be cleaned between uses with different patients.

According to a first aspect of the invention, there is provided a disposable x-ray side marker comprising a non-metallic material having a sufficiently high linear attenuation coefficient to be radiographically visible.

The skilled person will appreciate that a side marker necessarily includes one, and only one, of a left side indicator and a right side indicator. Other identifying information (e.g. a date, patient reference, front or back reference, clinician reference or the likes) may or may not additionally be present.

A left side indicator may be an "L"—the side marker may be L-shaped, or may comprise an L-shaped region of a different degree of radiopacity from its surroundings (e.g. a thicker or thinner portion, a portion made of a different material, or a hole).

A right side indicator may be an "R"—the side marker may be R-shaped, or may comprise an R-shaped region of a different degree of radiopacity from its surroundings (e.g. a thicker or thinner portion, a portion made of a different material, or a hole).

Advantageously, disposable markers may reduce the risk of cross-contamination between patients in clinical imaging contexts.

The material may be mouldable, and optionally may remain mouldable even when the marker is in use.

The skilled person will appreciate that what linear attenuation coefficient is sufficiently high for the material to be radiographically visible will depend on the thickness of the material (the thicker the material, the more radiographically visible it is, in general), but also that usability of a marker imposes a limit on marker thickness (too thick a marker would be awkward, heavy, take up additional storage space, and potentially be uncomfortable for a subject).

The following are provided as examples of what may constitute a sufficiently high linear attenuation coefficient to be radiographically visible with current technology:

The material may have an (average) atomic number greater than or equal to 11;

The material may have a linear attenuation coefficient greater than that of mammalian soft tissue;

The material may have a density greater than or equal to 1.5 g/cm$^3$ and preferably greater than or equal to 2 g/cm$^3$;

The material may have an (average) atomic mass number greater than or equal to 20, and preferably greater than or equal to 22;

The material may be gypsum.

The marker may comprise gypsum. Optionally, the gypsum may be the main or only x-ray attenuating material of the marker.

The marker may comprise a mineral (a solid, optionally naturally occurring, inorganic substance.) The mineral may be non-metallic. The mineral may be in the form of a powder, optionally mixed with a binder. The mineral may be the main or only x-ray attenuating material of the marker.

Advantageously, as the gypsum is not fired in some embodiments, the required energy input to form the marker may be lower than if it were fired. The energy cost, and so also the financial cost, may therefore be reduced. The marker may therefore be more environmentally friendly than otherwise.

The material may have a density smaller than that of metals, for example smaller than 7 g/cm$^3$.

Advantageously, having an x-ray attenuation lower than that of metals may mean that soft tissue is obscured to a lesser extent in radiographic images using the marker than with traditional metal markers.

The skilled person will appreciate that, in current digital x-ray imaging systems, overall image quality can be degraded when a metallic x-ray marker (or other metal or metallic object) is present at the edge of the image. Current software can struggle to process images in such cases, leading to a lower quality image in all areas due to difficulties in handling the affected area.

Advantageously, having a marker with an x-ray attenuation lower than that of metals may mean that, when a digital radiographic system is in use, the negative effect of a marker being placed partly outside the x-ray beam/on an edge of the imaged area is reduced.

The marker may comprise a core at least partially surrounded by a sealing layer.

The core may be made of gypsum.

In embodiments with a sealing layer, the sealing layer may be arranged to act as a mould for casting of the core, and the core may be arranged to be retained within the mould.

In such embodiments, the sealing layer may comprise paper. Optionally, the paper is die-cut or moulded to form a shaped mould for the core.

The sealing layer may comprise a coating of a protective material on the core.

The protective material forming the sealing layer may comprise at least one of latex, a resin, or a wax.

The protective material may be biodegradable.

The sealing layer may comprise a dip-coated layer.

The marker may comprise a ceramic and/or clay as the, or a, x-ray attenuating material.

The marker may comprise no transition metals and/or heavy metals.

According to a second aspect of the invention, there is provided a method of making a disposable x-ray side marker with no substantial metallic component. The method comprises:
    forming a mould out of a first material, the first material having a low linear attenuation coefficient;
    at least partially filling the mould with a second material, the second material having having a sufficiently high linear attenuation coefficient to be radiographically visible; and
    covering the filled mould with the first material.

The first material may be paper.

The second material may be or comprise gypsum.

The first material used to cover the filled mould may be either:
    (i) provided as a separate sheet sized to fit the mould; or
    (ii) formed from a foldable part of the mould.

According to a third aspect of the invention, there is provided a method of making a disposable x-ray side marker with no substantial metallic component. The method comprises:
    forming a core out of a core material having having a sufficiently high linear attenuation coefficient to be radiographically visible;
    coating the core in a protective material so as to form a sealing layer which at least partially surrounds the core.

The core material may be mouldable.

The core material may be or comprise gypsum.

The protective material may be or comprise latex, wax, and/or a resin.

The coating may be performed by dip-coating.

In embodiments with gypsum or another curable material as the core, the method may comprise allowing the core material to cure rather than firing it. Advantageously, this may reduce the energy required for manufacture.

According to a fourth aspect of the invention, there is provided use of a disposable x-ray side marker as described with respect to the first aspect of the invention as an x-ray marker.

According to a fifth aspect of the invention, there is provided use of a non-metallic material as an x-ray attenuating material in an x-ray marker.

The non-metallic material may be the main or only x-ray attenuating material in the x-ray marker.

The non-metallic material may be mouldable.

The non-metallic material may be gypsum. The gypsum may be unfired.

The gypsum may be at least partially surrounded by a sealing layer.

According to a sixth aspect of the invention, there is provided a method of marking a radiographic image of a subject, taken by an x-ray imaging apparatus, the method comprising:
    positioning at least one x-ray side marker as described with respect to the first aspect of the invention near the subject and at least partially within a view area of the imaging apparatus;
    recording the image whilst the x-ray side marker is in position.

The x-ray side marker may be attached to the subject.

The subject may be a person.

The x-ray side marker may be arranged to be worn by, or attached to clothing of, the person.

The method may comprise disposing of the x-ray marker once imaging of the subject is complete. Advantageously, this may reduce the chance of cross-contamination.

According to a seventh aspect of the invention, there is provided a disposable x-ray marker comprising gypsum.

The gypsum may be the main or only x-ray attenuating material of the marker.

The marker may be a side marker.

According to an eighth aspect of the invention, there is provided a disposable x-ray marker comprising a mineral powder mixed with wax.

The mineral powder/wax blend may be the main or only x-ray attenuating material of the marker.

The mineral powder may be or comprise one or more minerals from the following list:
    gypsum
    bentonite clay
    salt
    graphite
    bronze powder
    brass powder
    iron powder
    iron filings
    sodium bicarbonate
    egg shells The mineral powder may be non-metallic.

The wax may be or comprise beeswax.

The wax may be or comprise soy wax or paraffin wax.

The marker may be a side marker.

According to a ninth aspect of the invention, there is provided a disposable x-ray marker comprising a mineral powder contained within a mould.

The mould may be or comprise paper and/or a polymeric material.

The powder may be a loose (e.g. being uncured/unfired) powder, held in place by the mould.

The skilled person would understand that features described with respect to one aspect of the invention may be applied, mutatis mutandis, to the other aspect of the invention.

There now follows, by way of example only, a detailed description of embodiments of the present invention with reference to the accompanying drawings in which.

Figure 1A:
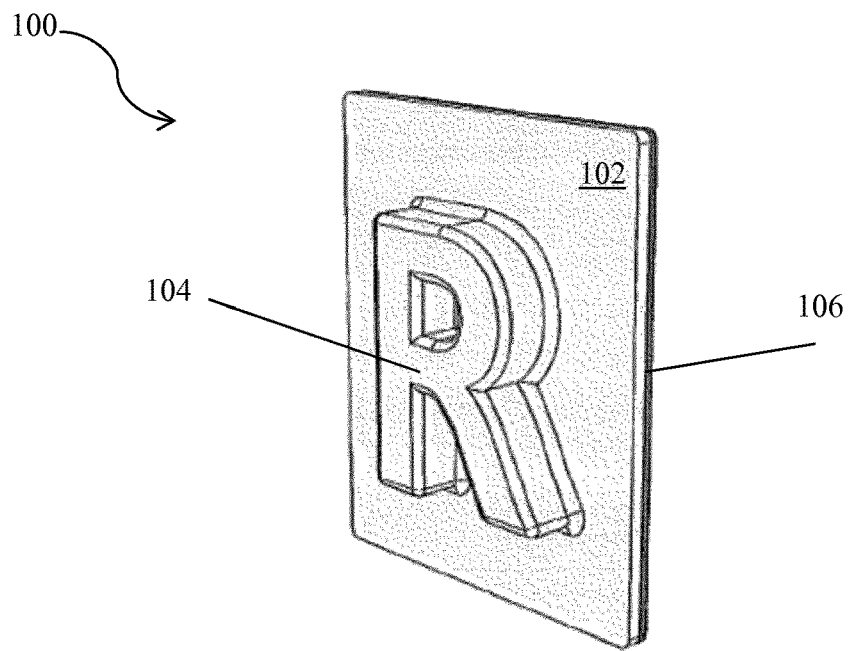
FIG. 1A is a schematic representation of an x-ray marker of an embodiment.
Figure 1B:
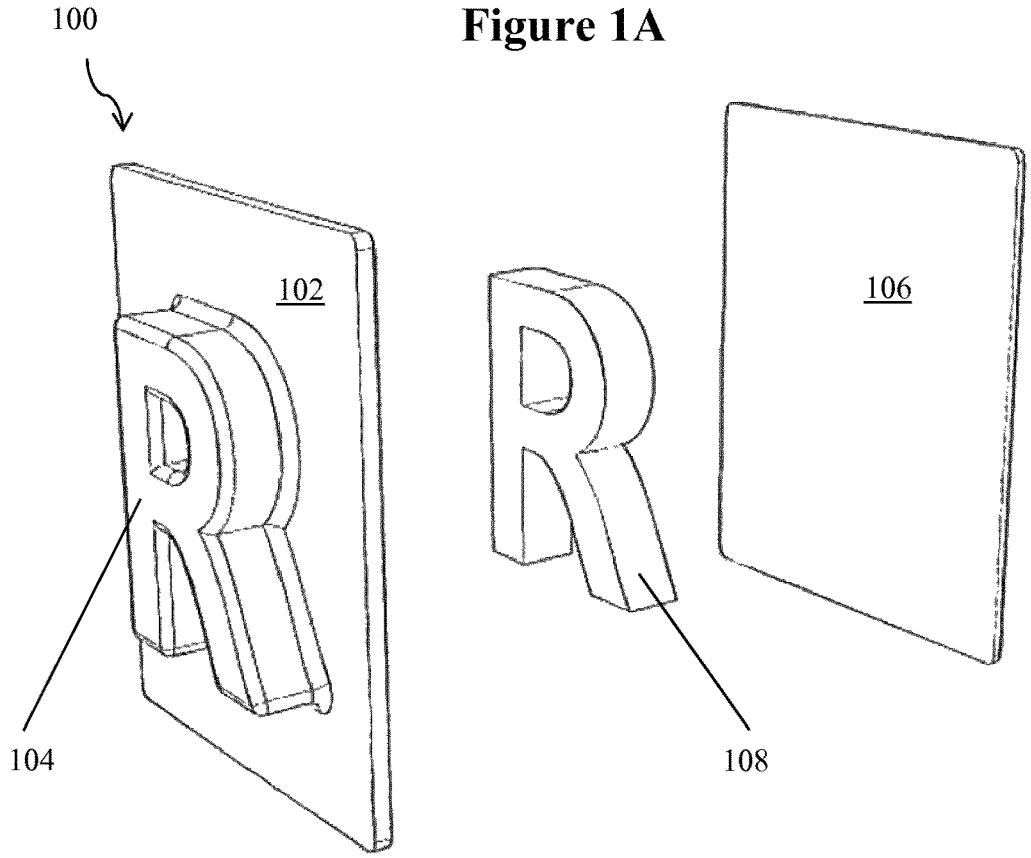
FIG. 1B is an exploded view of the x-ray marker of FIG. 1A.
Figure 3:
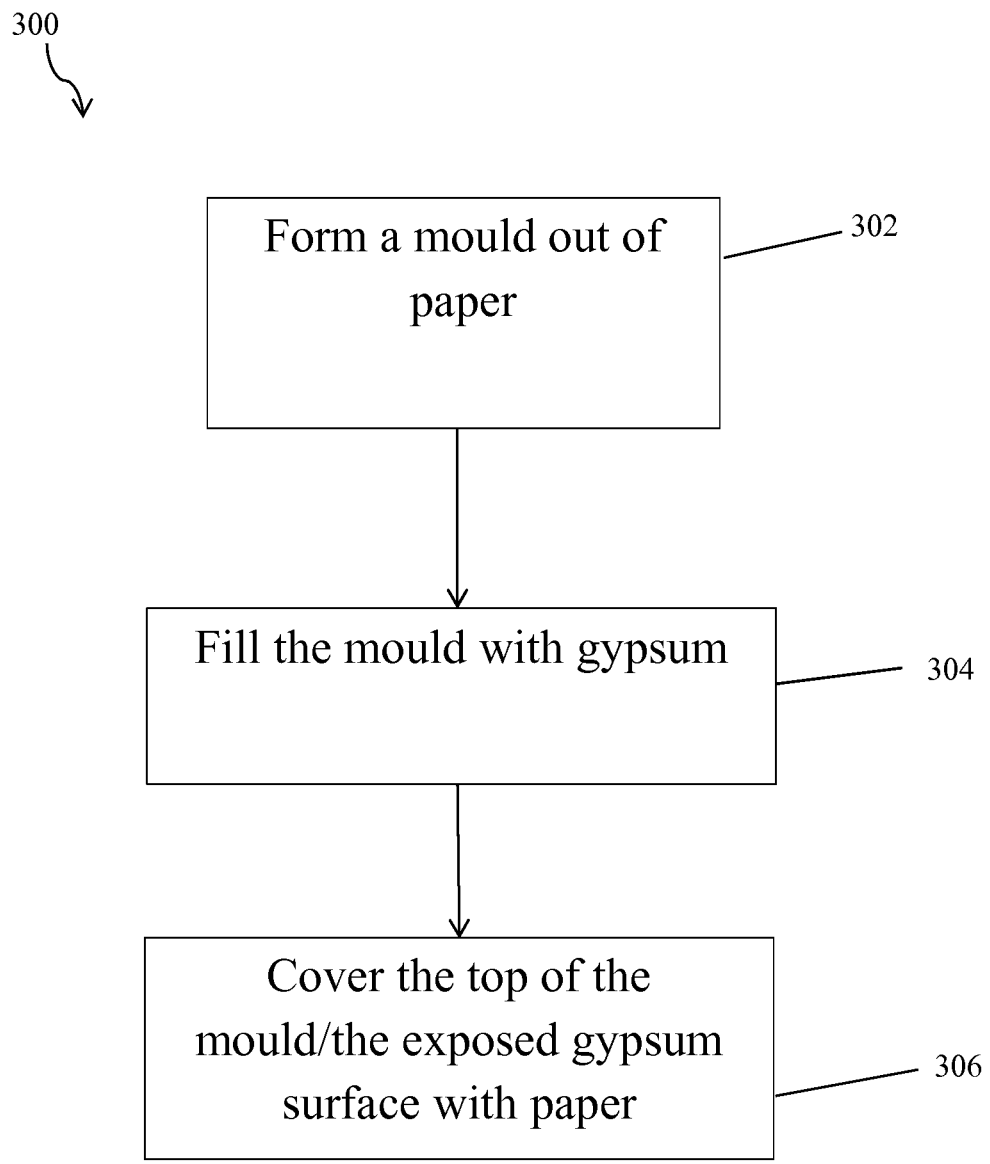
Figure 4A:
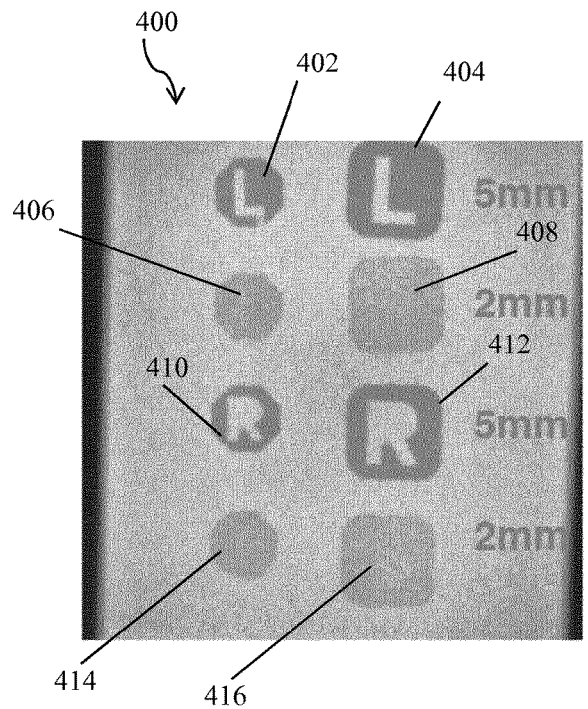
Figure 4B:
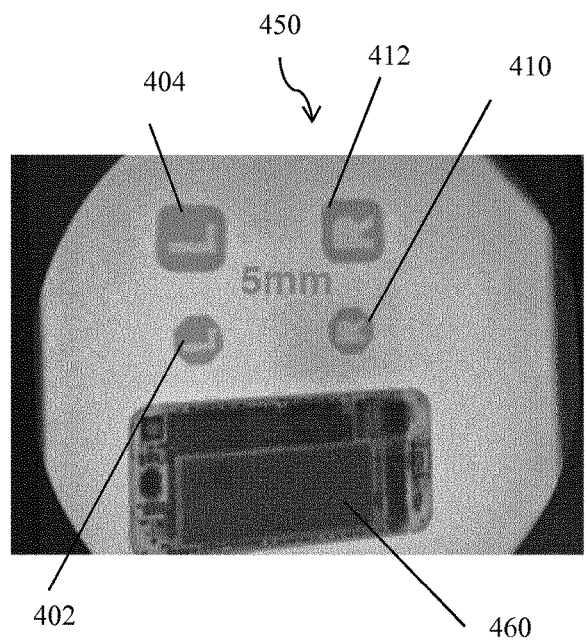
Figure 5A:
Figure 5B:
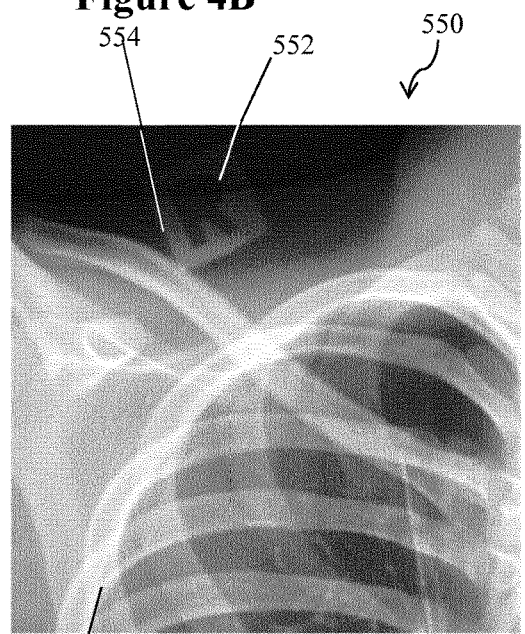
Figure 6A:
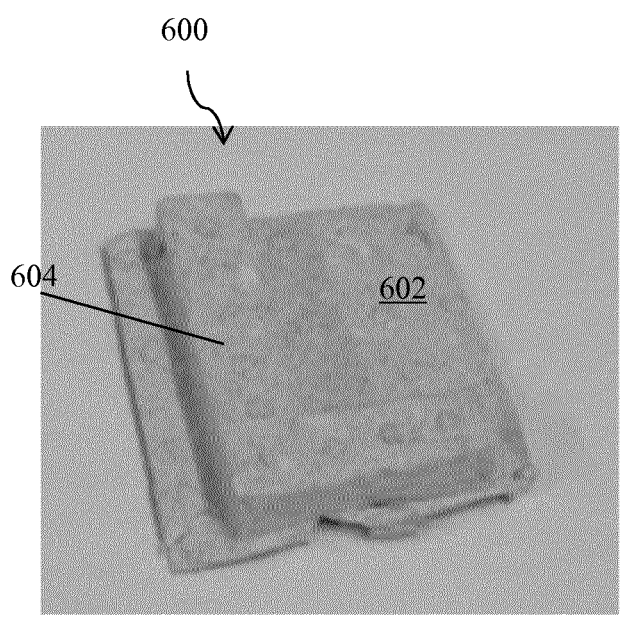
Figure 6B:
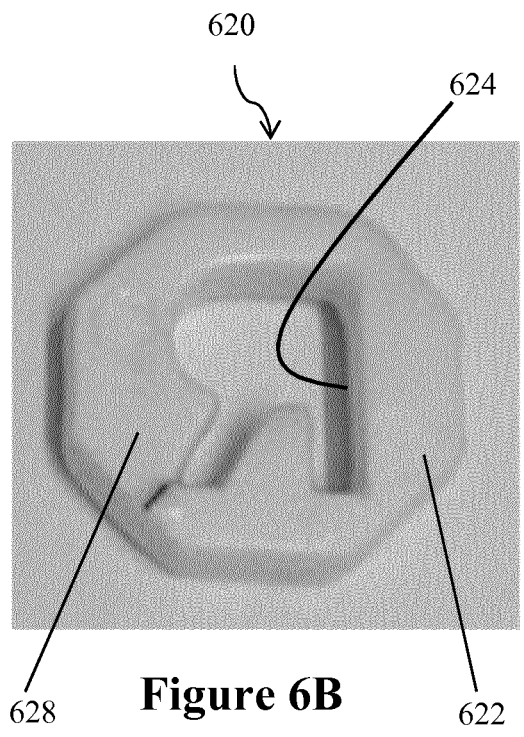
Figure 6C:
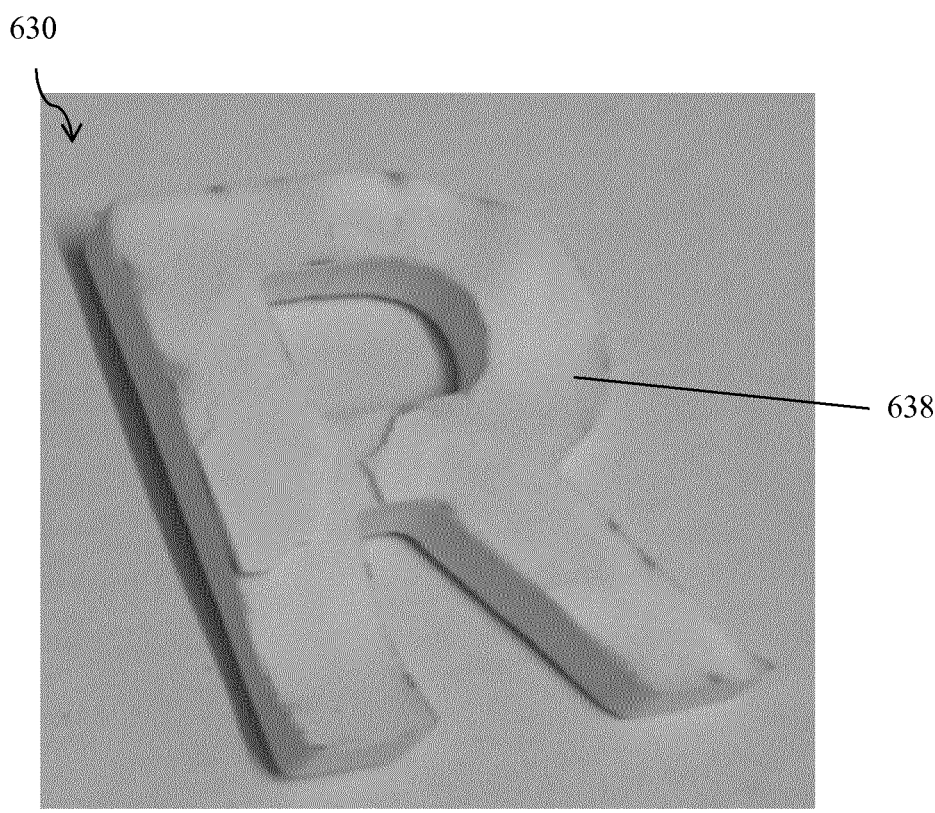
Figure 7:
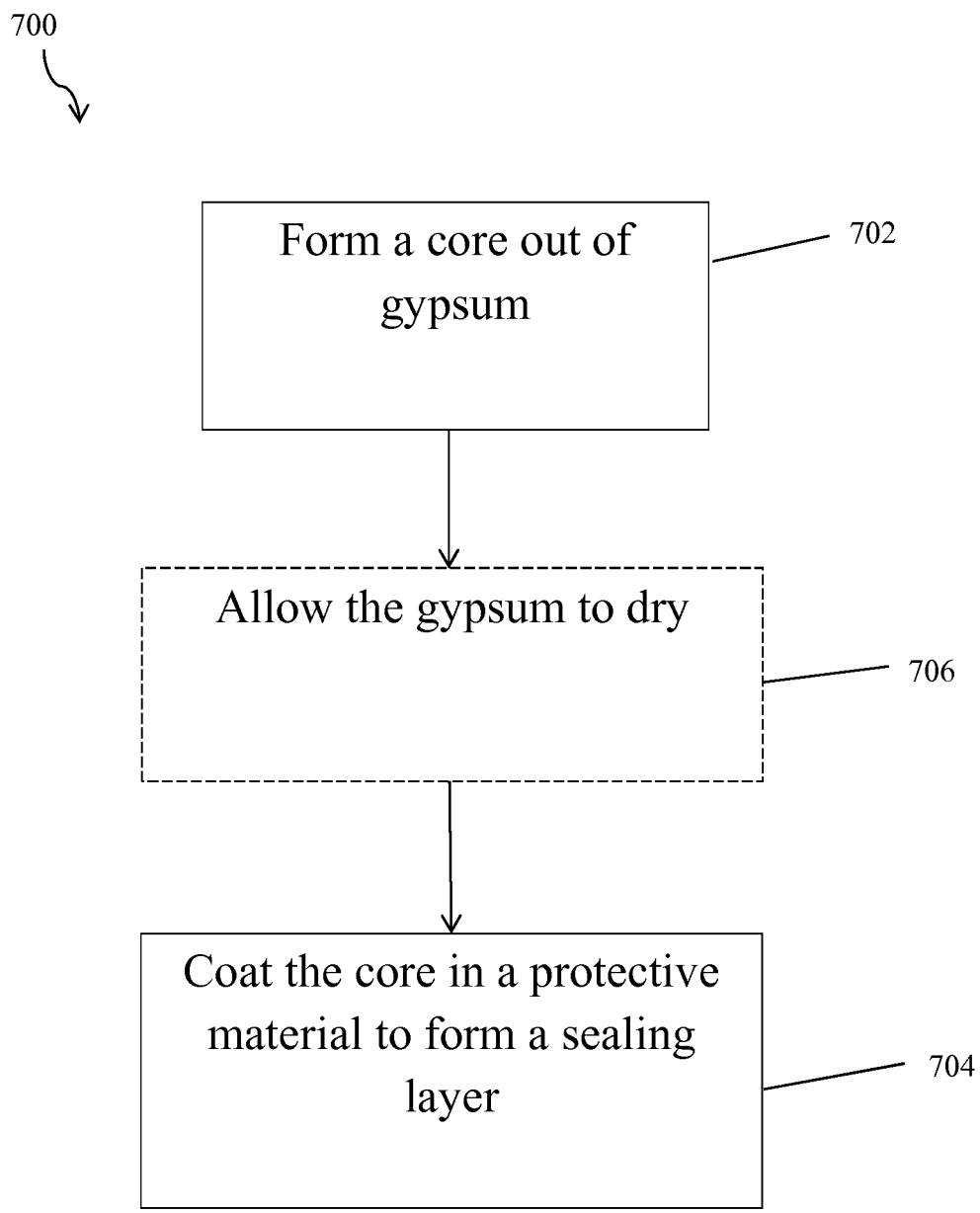
Figure 8:
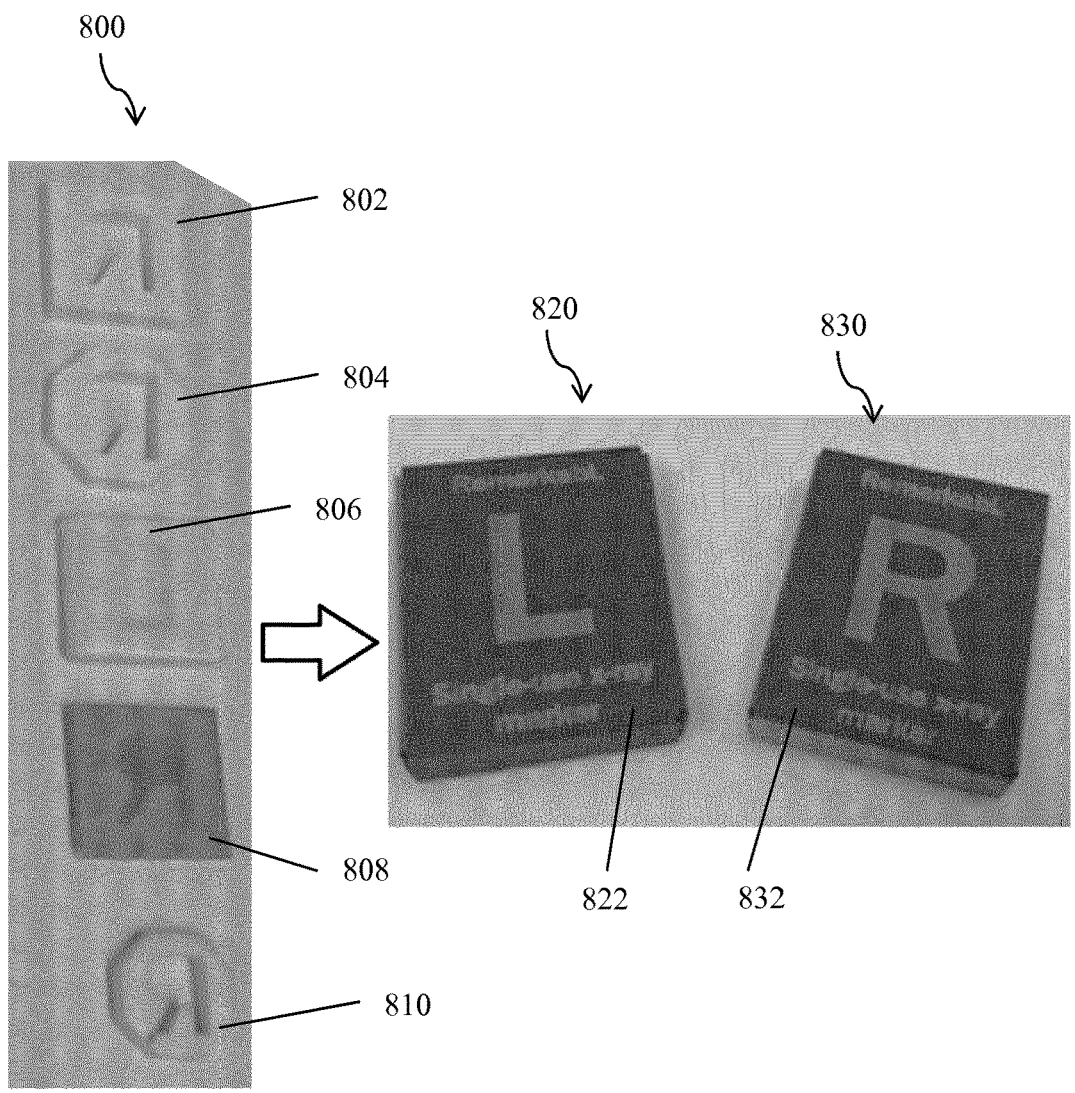
Figure 9:
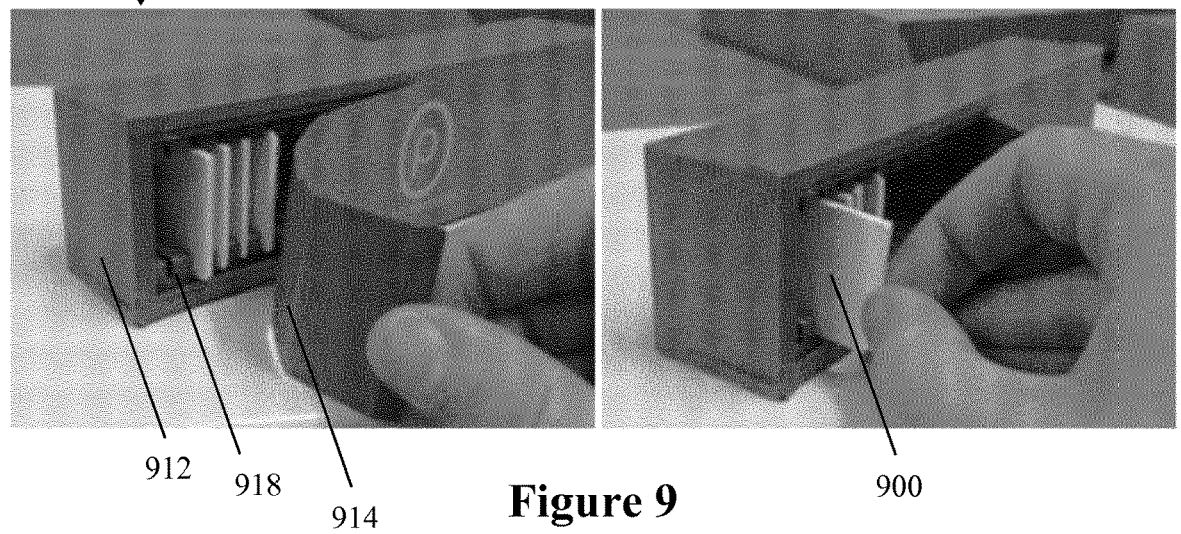
Figure 10A:
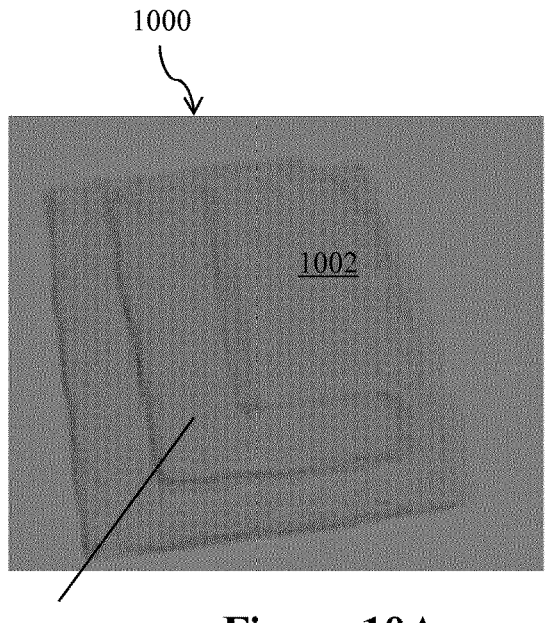
Figure 10B:
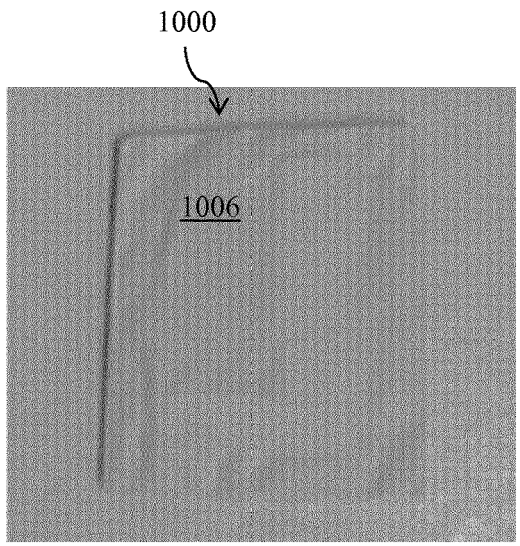
Figure 11A:
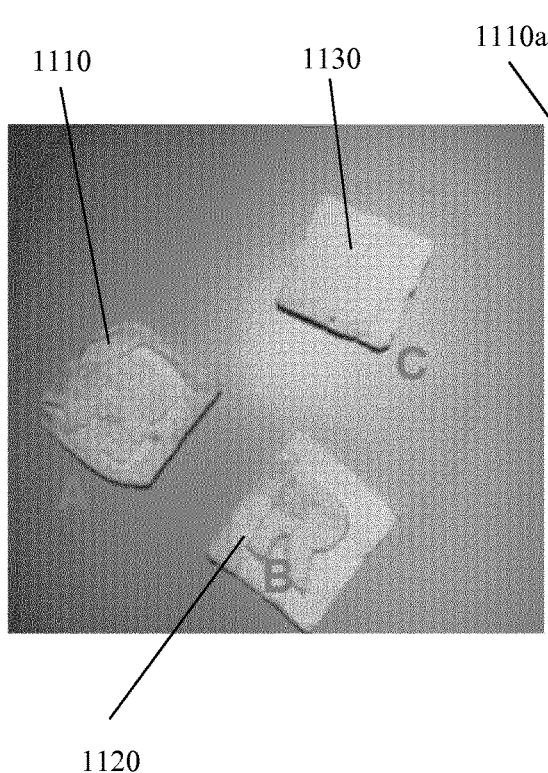
Figure 11B:
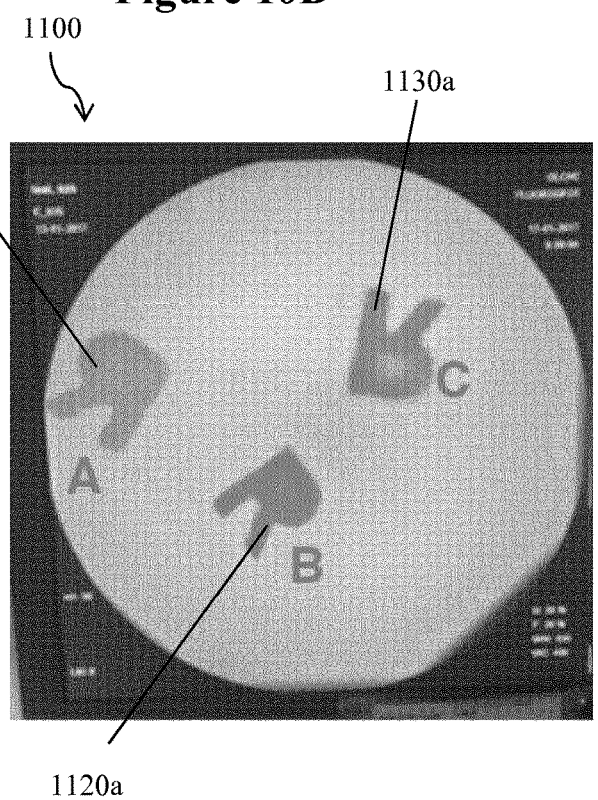
Figure 12:
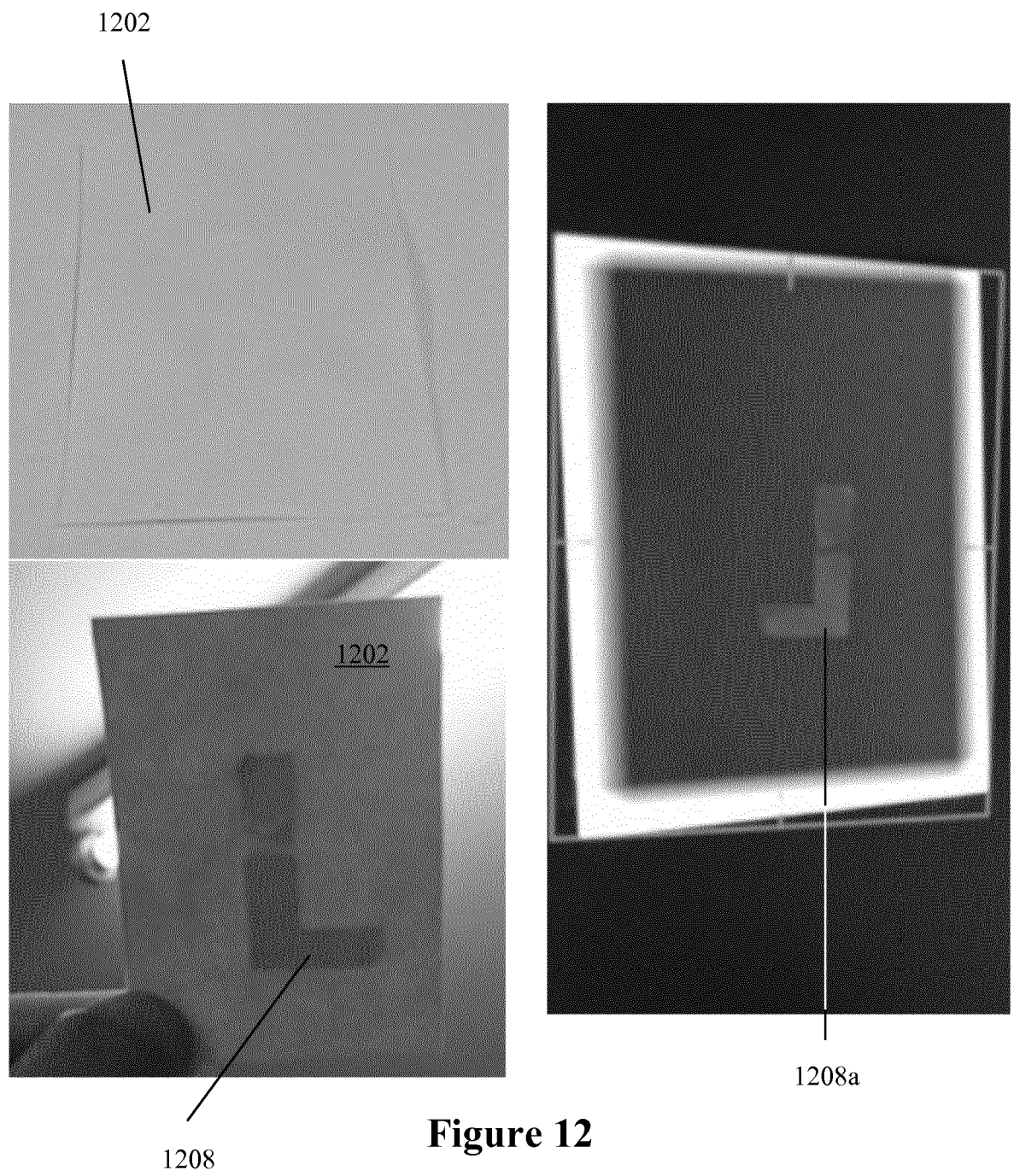
Figures 13A, 13B:
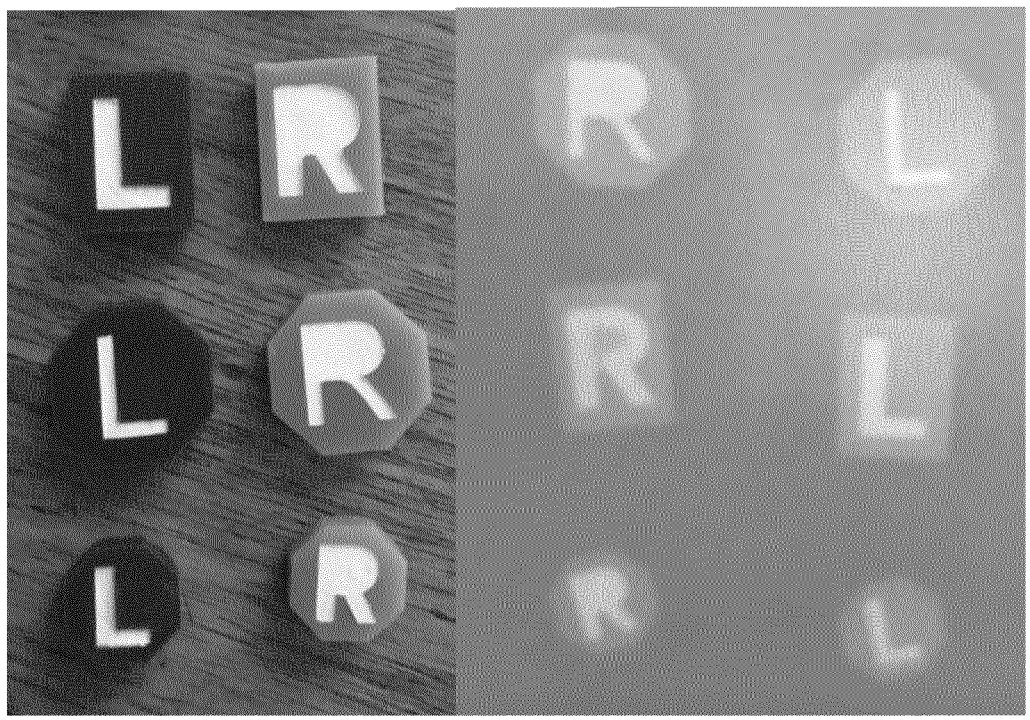
Figure 14:
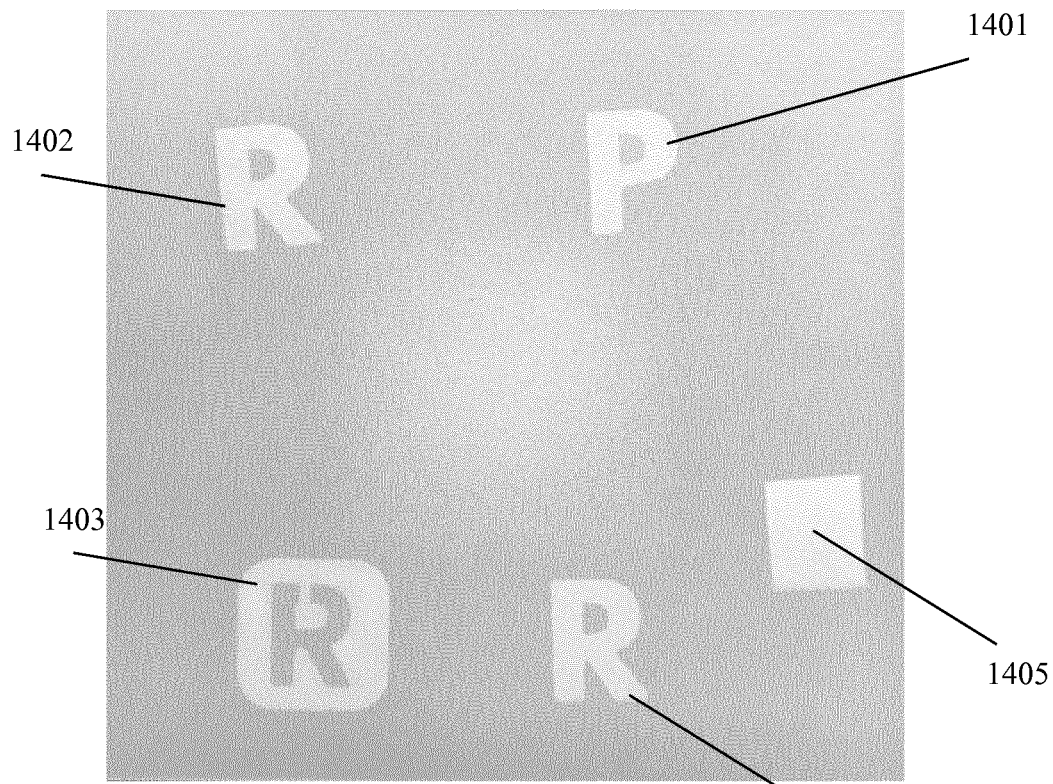
Figure 15:
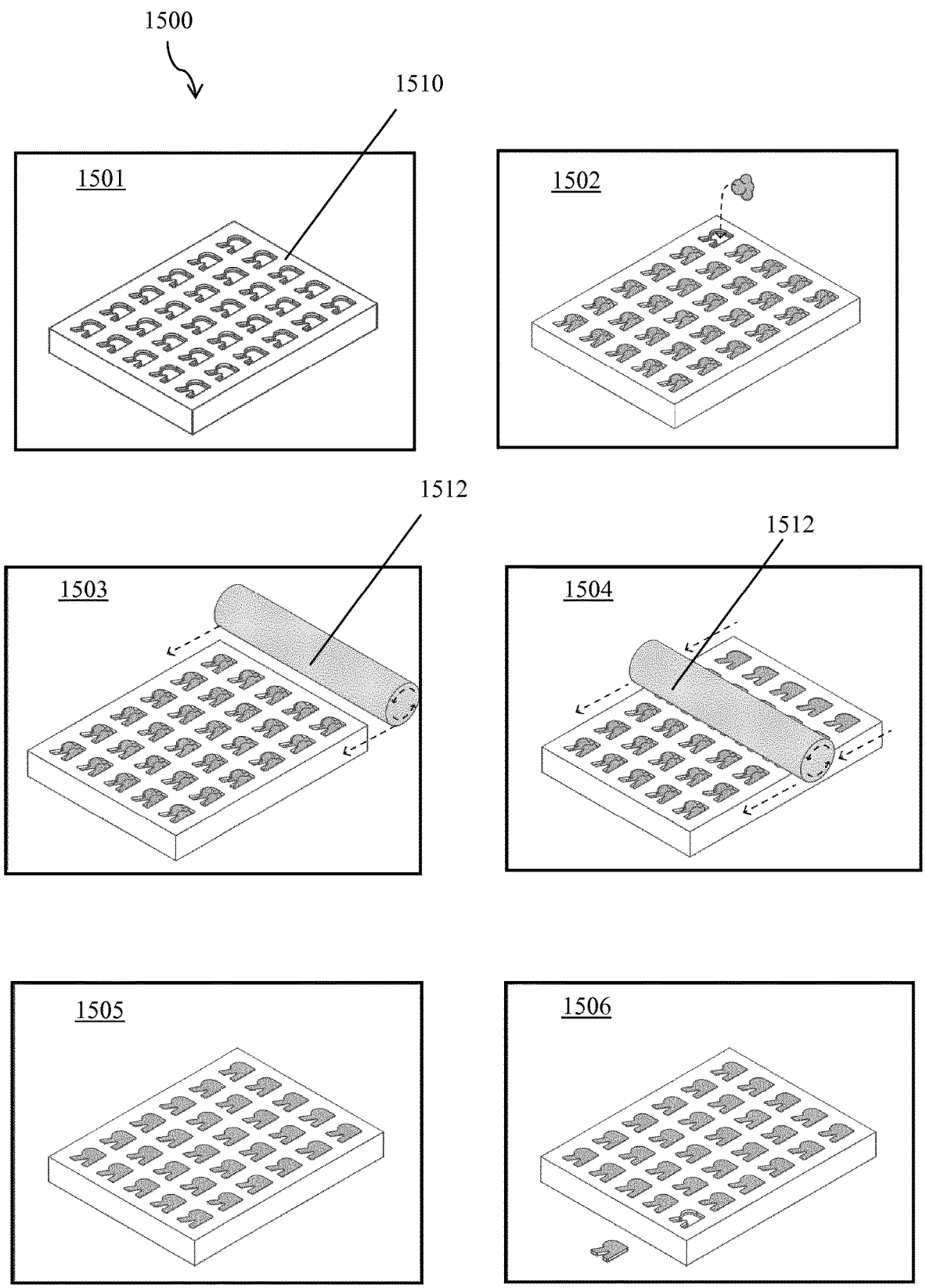
Figure 16:
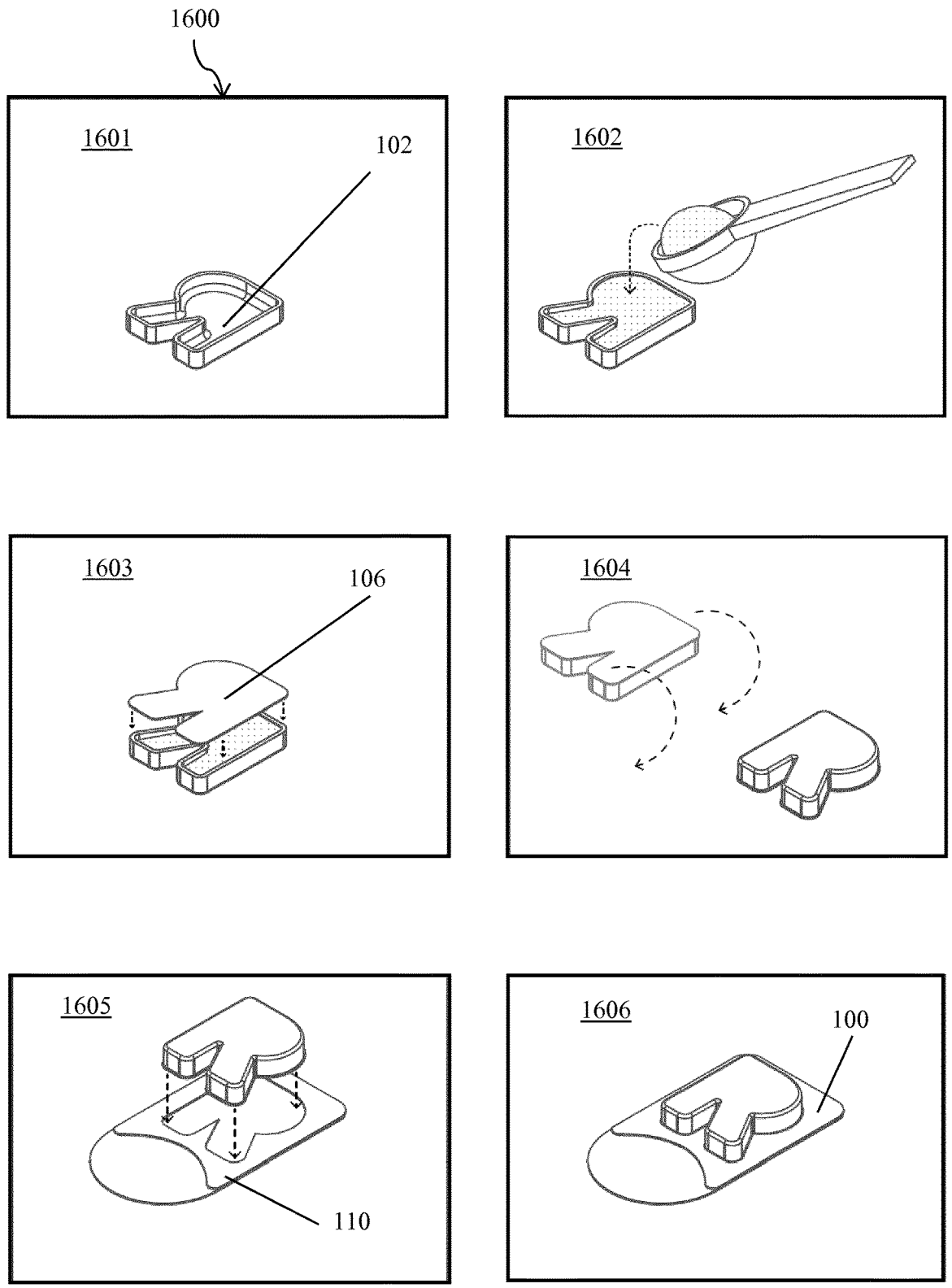

FIGS. 2A to 2C provide cross-sectional, plan and side views of the marker of FIGS. 1A and 1B;

FIG. 3 illustrates a method of making an x-ray marker as shown in the preceding figures;

FIGS. 4A and 4B show radiographic images of markers of various embodiments, with an X-ray image of a mobile phone provided for reference;

FIGS. 5A and 5B show x-ray images taken using markers of an embodiment;

FIGS. 6A to 6C are photographs of markers of various embodiments;

FIG. 7 illustrates a method of making an x-ray marker according to various embodiments;

FIG. 8 illustrates markers of various embodiments alongside suitable packaging therefor;

FIG. 9 shows a box of markers of an embodiment of the invention;

FIGS. 10A and 10B show plan and underneath views of a marker of an embodiment;

FIG. 11A shows three markers of embodiments;

FIG. 11B shows a radiographic image of the three markers shown in FIG. 11A;

FIG. 12 shows a marker of another embodiment;

FIG. 13A shows left and right side markers formed of gypsum cast in beeswax;

FIG. 13B shows a radiographic image of the side markers shown in FIG. 13A;

FIG. 14 shows a radiographic image of side markers made using five different material blends;

FIG. 15 illustrates a method of casting X-ray markers using a re-useable mould; and FIG. 16 illustrates a method of making X-ray markers using a single-use mould.

FIGS. 1A and 1B illustrate a disposable x-ray marker 100 according to an embodiment of the invention.

The marker 100 comprises a shaped region 104. In the embodiment being described, the shaped region 104 is R-shaped and may be used, for example, to indicate the right-hand side of a subject of a radiographic image. The skilled person will appreciate that other shapes may be used, including letters, numbers, and/or other designs.

In the embodiment being described, the marker 100 is a side marker, and more specifically a right side marker.

In the embodiment being described, a first face 102 of the marker 100 is provided by a shaped layer of material, in this case papier-mâché (moulded pulp paper). The skilled person will appreciate that other materials, such as paper, cardboard, wood, or plastic could be used in additional or alternative embodiments.

The first face 102 is shaped to provide a covering layer of the shaped region 104. In the embodiment being described, the first face 102 is arranged to be the front face of the marker 100.

In the embodiment being described, a second face 106 of the marker 100 is provided by a sheet of material, in this case a substantially flat sheet of paper. The skilled person will appreciate that other materials, such as cardboard, wood or plastic could be used in additional or alternative embodiments. In the embodiment being described, the second face 106 is arranged to be the rear face of the marker 100.

In the embodiment being described, a core 108 is provided between the first face 102 and the second face 106. The core 108 fits within the shaped region 104.

In the embodiment being described, the core 108 is made of gypsum. The skilled person will appreciate that any material sufficiently x-ray attenuating to show up on a radiographic image may be used for the core.

In the embodiment being described, the core 108 is made of unfired gypsum. Advantageously, the energetic and financial costs associated with firing are therefore avoided.

In the embodiment being described, the first 102 and second 106 faces are sealed together so as to contain the core 108. The skilled person will appreciate that unfired gypsum can be powdery to the touch, and that the first 102 and second 106 faces provide a sealing layer which encloses and protects the gypsum core 108.

FIGS. 2A and 2B show additional views of the marker 100 of the embodiment being described.

In this embodiment, the first and second faces 102, 106 are substantially rectangular, with a width, Y, of 30 mm, and a height, X, of 35 mm. The skilled person will appreciate that the selected size and shape may vary depending on various factors, which may include the size of the subject to be radiographed and the number of markers 100 to be used.

In the embodiment being described, the marker 100 has a width, Z, of between 2 mm and 10 mm, preferably between 3 mm and 8 mm, and in this case more specifically of 6 mm.

The skilled person will appreciate that the core 108 needs to be sufficiently thick for the core 108 to show up on a radiograph, and that a minimum required thickness will depend on the attenuation of the material from which the core 108 is made. The marker 100 is therefore arranged to be wide enough to accommodate the core 108.

FIG. 3 illustrates a method 300 of making the marker 100 shown in the preceding figures.

A mould 102 is formed 302 out of paper. The mould 102 is arranged to form the first face 102 of the marker 100. In the embodiment being described, the paper is pulped and moulded to form the front face 102 with a shaped region 104. In the embodiment being described, the front face 102 is substantially rectangular and surrounds the shaped region 104. In additional or alternative embodiments, the front face 102 may take the form of the shaped region 104 with a rim to allow a back face 106 to be attached thereto. In additional or alternative embodiments, the front face 102 may be square, circular, hexagonal, irregular in shape, or may take any other suitable shape.

The mould 102 is then filled with gypsum. The gypsum dries to form the core 108.

The top of the mould 102 is then covered with a sheet of paper 106, which forms the second face 106 of the marker 100. In the embodiment being described, the second face 106 is glued to the first face 102. In additional or alternative embodiments, any other suitable sealing means, such as staples, stitching, sticky tape, clips or the like, may be used.

The core 108 is therefore contained within the first and second faces 102, 106.

FIGS. 10A (front view) and 10B (back view) illustrate a left side marker 1000 made using the method 300 of FIG. 3. The mould 1002 is made of papier-mâché and the second face/backing sheet 1006 is provided by a sheet of paper arranged to be adhered to the back of the mould 1002 once the shaped portion 1004 has been filled. In the embodiment shown, the shaped portion 1004 is filled with gypsum with a thickness of 2 mm. The papier-mâché provides a hard, protective shell to protect the gypsum core.

FIG. 11A illustrates three right side markers 1110, 1120, 1130 made using the method of FIG. 3. The core of the left-most marker (A, 1110) is made from a blend of sodium bicarbonate and gypsum, whereas the cores of the other two markers (B, C—1120, 1130) are made from pure gypsum mixed with water. The skilled person will appreciate that the gypsum/gypsum blend letters may be pre-cast and then inserted into the moulds, or that the material (including water) may be poured into the mould to form the letter in the mould.

In the embodiments shown in FIG. 11, the moulds used are pressed paper moulds rather than papier-mâché moulds.

FIG. 11B shows radiographic images 1110a, 1120a, 1130a of the three markers 1110, 1120, 1130, respectively. The paper portion of each marker 110-1130 is invisible in the x-ray image.

FIGS. 4A and 4B show radiographic images 400, 450 including markers 402-416.

The image 400 in FIG. 4A illustrates right ("R") and left ("L") markers. In the embodiments shown, the gypsum takes the form of a shape (an octagon 402, 410 or a square with curved corners 404, 412) with a cut-away letter, instead of the form of a letter. The skilled person will appreciate that marking may therefore be provided by a shaped absence of higher linear attenuation material.

The top two markers 402, 404 are left markers of two different sizes, each made using a 5 mm thick piece of cast gypsum. Two pieces 406, 408 of 2 mm thick gypsum are shown below to illustrate the effect of thickness on visibility in a radiographic image.

The next two markers 410, 412 are right markers of two different sizes, each made using a 5 mm thick piece of cast gypsum. Two pieces 414, 416 of 2 mm thick gypsum are shown below to illustrate the effect of thickness on visibility in a radiographic image.

It can be seen that the 5 mm thick gypsum 402, 404, 410, 412 gives a clearer radiographic image than the 2 mm thick gypsum 406, 408, 4141, 416.

FIG. 4B shows a radiographic image 450 with the left and right markers 404, 404, 410, 412 shown in FIG. 4A alongside a mobile phone 460. The skilled person will appreciate that mobile phone materials range from metal (high density and black on the image 450) to plastic (low density and not visible on image 450).

The total linear attenuation coefficient (μ) of a material determines how much of an x-ray beam travelling through the material is transmitted to the other side. The amount of an x-ray beam transmitted through a material, relative to that transmitted through adjacent materials, determines how well the material is seen on the resultant image (radiograph). The linear attenuation coefficient is impacted by both the density of the material (g/cm$^3$) and the atomic number (for pure elemental materials), or average atomic number (for composite materials), of the material.

The skilled person will appreciate that, when the average atomic number is calculated, the average chosen is generally the mean. Median or modal values may be used in some embodiments.

Atomic number is the number of protons in an atom. The skilled person will appreciate that atomic mass, i.e. the number of protons and neutrons in an atom, also has an effect on x-ray absorption, and that an atomic mass of 22 or greater may be preferred in some embodiments.

The thicker the piece of material used, the more the x-ray beam will be attenuated. A material needs to be sufficiently dense and have a sufficiently high atomic number in order to be radiographically visible without the item having to be overly thick.

The skilled person will appreciate that practicalities in use may determine a maximum thickness; for example, portability and ease of use.

The skilled person will appreciate that, in some uses, a person being imaged may be asked to lie down with the marker underneath them. The marker should therefore be thin enough to not significantly change the person's position, nor make that person uncomfortable.

The skilled person will appreciate that, for ease of use, a radiographic marker preferably has a thickness of below 5 cm, more preferably below 2 cm, and more preferably around or below 1 cm.

For ease of handling, a minimum marker thickness of 2 mm to 5 mm is chosen in various embodiments. In some embodiments, a maximum marker thickness of 5 mm to 10 mm is selected. In some embodiments, marker thickness is between 2 mm and 15 mm, and for example may be between 2 mm and 5 mm, between 3 mm and 10 mm or between 5 mm and 15 mm.

The skilled person will appreciate that software handling of the data may also have an effect, along with screen resolution etc.

Gypsum markers 404, 404, 410, 412 (at around 2.3 g/cm$^3$) look different from metal (at around 7.8 g/cm$^3$) in radiographs, as gypsum is not as dense so does not have the same visibility in a radiograph. However, gypsum 404, 404, 410, 412 markers are still sufficiently dense to be seen when used in a suitable thicknesses—by contrast, paper has a density of around 0.9 g/cm$^3$ and is not sufficiently dense for use as a marker. The chosen thickness is also influenced by needing the markers 404, 404, 410, 412 to be sufficiently robust in most embodiments.

The skilled person will appreciate that materials other than gypsum can be used—for example, sodium bicarbonate, and mixtures of sodium bicarbonate and gypsum, have also been shown to offer sufficient linear attenuation to x-rays to show up clearly in radiographic images. For the same marker thickness, gypsum was shown to have a higher attenuation than gypsum-sodium bicarbonate mixes. Materials with a high sugar and glucose content (such as mint sweets) were also shown to be radiographically visible, although less distinct than a 100% gypsum marker of the same thickness.

FIGS. 5A and 5B show radiographic images 50, 550 of markers 502, 552 alongside a human subject. The skilled person will appreciate that bone 506, 556 has a relatively high linear attenuation and shows up clearly on radiographic images (white or light grey, in the images 500, 550 shown). By contrast, soft tissue 504, 554 is has a lower linear attenuation and does not show up as clearly.

The markers 502, 552 used for these images 500, 550 comprise a 5 mm thick cast gypsum core 108. As can be seen from the image, the markers 502, 552 have a lower linear attenuation than bone 506, 556 (and hence not as bright in the image 500, 500). The markers 502, 552 have a higher linear attenuation than soft tissue 504, 506 and therefore show up more clearly in the radiograph.

FIG. 5B illustrates a marker 552 overlapping soft tissue 554. The skilled person will appreciate that the linear attenuation is low enough to not obstruct the outline of the soft tissue 554—unlike a metal marker, which would be bright enough that any differentiation due to soft tissue would be lost, a lighter grey area can be seen where there is overlap of the marker 552 and the soft tissue 554.

FIGS. 6A-6C show markers 600, 620, 630 according to various alternative embodiments.

FIG. 6A shows a marker 600 made using a first layer 602 which was formed using papier-mâché in a plastic 3D-printed mould. The shaped region 604 is L-shaped and accommodates an L-shaped gypsum core.

FIG. 6B shows a marker 620 made from a shaped core 628 with a letter-form (R) hole 624. The marker 620 is covered with a sealing layer 622 of a plastics material. In this embodiment, the plastics material is latex and the sealing layer 622 is formed by dip-coating the core 628 in latex. The skilled person will appreciate that other coating materials (for example resins or waxes) and/or methods (for example, brush-painting or spraying) may be used in additional or alternative embodiments.

FIG. 7 illustrates the method 700 used to form markers 620 of some embodiments, including that shown in FIG. 6B

A core is formed 702, in this case out of gypsum. The gypsum is then allowed to dry 706 (in some embodiments, step 706 may be replaced with, or followed by, a firing step). The dried core is then coated 704 in a protective material so as to form a sealing layer.

In the embodiment shown in FIG. 6B, the core 628 is completely encased by the sealing layer 622. Advantageously, this may make the marker 620 waterproof as well as reducing the chance of powder loss. The skilled person will appreciate that powder loss may be less of an issue for fired cores.

FIG. 6C shows a different kind of marker 630 in which shaped silk is placed into a mould which is then filled with the core material (in this case, gypsum). In this case, an R-shape was cut out of silk. The gypsum impregnates the silk and bonds with it to form the core 638. The resultant composite material core 638 may be stronger than gypsum alone. The skilled person will appreciate that different materials may be used instead of, or as well as, silk. Further, the resultant core 638 may then be coated or wrapped in a sealing layer. The silk may provide a protective layer on one or more sides of the core 638, and/or a strengthening layer within the core.

FIG. 8 demonstrates markers 800 of other embodiments, and packaging options 820, 830. The markers 800 shown are all made with gypsum cores.

The top marker 802 has a core thickness of 5 mm and a square outline, around an R-shaped hole.

The second marker 804 again has a core that is 5 mm thick with an R-shaped hole, but is octagonal instead of square in outline.

The third marker 806 again has a core that is 5 mm thick. The marker 806 has a square outline around an L-shaped hole. The marker 806 is wrapped in glassine paper—the glassine paper provides the sealing layer.

The fourth marker 808 has a core that is 3 mm thick. The marker 808 has a square outline around an R-shaped hole. The marker 808 is wrapped in gummed paper tape—the gummed paper tape provides the sealing layer.

The bottom marker 810 has a core that is 3 mm thick. The marker 810 has an octagonal outline around an R-shaped hole. The marker 810 is dipped in latex to form the sealing layer.

The right-hand side of FIG. 8 shows two packaged markers 820, 830.

The left-hand marker 820 shows a red box 822 with a front cover having a printed label stating a brand name, "L", and "Single-use X-ray marker". The "L" indicates the shape of the core (or the shaped hole of the core) of the marker contained therewithin. The colour red is used as this is traditionally used in the field for left-hand markers.

The right-hand marker 830 shows a green box 832 with a front cover having a printed label stating a brand name, "R", and "Single-use X-ray marker". The "R" indicates the shape of the core (or the shaped hole of the core) of the marker contained therewithin. The colour green is used as this is traditionally used in the field for right-hand markers.

The skilled person will appreciate that colour, shape, text etc. may vary and that FIG. 8 is provided by way of example only.

FIG. 9 shows another packaging option 950 for disposable markers 900. A box 912 is provided with a lid 914. In the embodiment shown, the box 912 and lid 914 are both made of paper or cardboard; the skilled person will appreciate that different materials may be used in other embodiments. The lid 914 is arranged to peel off the box 912 when pulled, so allowing the box 912 to be gradually opened to a greater extent as the markers 900 are used up. The box 912 and lid 914 may serve to protect the markers during transit.

The inside of the box 912 is provided with grooves 918 arranged to hold markers 900.

The skilled person will appreciate that many different forms of packaging may be provided in other embodiments.

FIG. 12 illustrates a left side marker formed from a thin gypsum letter embedded in a sheet of paper. In the embodiment being described, the letter is a 0.3 mm thick cast gypsum letter 1208 embedded in 80 gsm paper 1202.

As illustrated on the left hand side of FIG. 12, the letter 1208 may be visible only when the paper 1202 is help up to a light.

The radiographic image 1208*a* on the right hand side of FIG. 12 illustrates that the embedded letter is clearly visible when x-rayed.

The skilled person would appreciate that markers of this type may be provided as a booklet of tear-off pages. Each page could have a letter 1208 embedded in it and could be disposed of easily after use.

Various other materials and material combinations or blends for markers 100 were tested.

FIG. 13A shows three left side markers and three right side markers. In the embodiments shown, the side markers comprise blocks of beeswax moulded to have an L- or R-shaped indentation, accordingly, with the indentation filled with a radiopaque substance; in this case gypsum. The skilled person will appreciate that other kinds of wax, and/or other radiopaque substances, may be used in other embodiments. The blocks are rectangular and hexagonal in the embodiments shown; the skilled person would appreciate that any appropriate shape may be used.

In the embodiments shown, beeswax with a red pigment added was used for the left side markers and beeswax with a green pigment added was used for the right side markers. The skilled person will appreciate that the different colours may reduce the chance of left and right side markers getting mixed up.

The skilled person will appreciate that, as well as being easy to mould, so facilitating manufacture, the beeswax blocks may hold and protect the cast letter, so reducing the likelihood of breakages and making the markers more stable during processing.

FIG. 13B shows an X-ray image of the side markers of FIG. 13A. As shown in the X-ray image, the radiopacity of the (pigmented) beeswax blocks is sufficient for the beeswax to show up in the image, although the image of the beeswax is substantially less bright (as the material is less radiopaque) than the gypsum letter.

The skilled person will appreciate that gypsum is relatively easy to cast, but that other materials (such as bentonite clay and powdered eggshells) may have greater radiopacities than gypsum but be less easy to cast. Two methods for handling such materials are discussed below. Blending the powdered materials with a polymer or other binding agent, such as beeswax, may facilitate moulding a side marker using the powdered material. Beneficially, the polymer or other binding agent may also contribute some radiopacity to the blend, as for the beeswax shown in FIG. 13B.

Blends of mineral powders with molten beeswax were tested to identify blends resulting in a stable, strong and sufficiently radiopaque material suitable for X-ray markers.

In one embodiment, pure (unpigmented) beeswax was blended with gypsum powder.

Weight ratios of wax to gypsum powder of around 2:3 (e.g. around 1:1.45-2.2 g of wax to 3.2 g of gypsum powder—or around 1:1.35-6.5 g of wax to 8.8 g of gypsum powder) were tested.

A radiographic image of a P-shaped marker 1401 made using a blend comprising 2.2 g of wax and 3.2 g of gypsum powder is shown in FIG. 14.

An R-shaped marker 1402 made of pure gypsum and of the same thickness as the P-shaped marker 1401 (around 3 mm) is also shown; the radiopacities can be seen to be similar from the brightness—the skilled person will appreciate that the relative brightness of objects in an X-ray image shows the relative radio-opacity.

A marker 1403 with an R-shaped hole is also pictured. This marker 1403 is made from gypsum cast with bronze powder and has a thickness of approximately 3 mm. The ratio of bronze to gypsum is around 1:10 by weight. The gypsum/bronze marker 1403 appears slightly brighter than the gypsum or gypsum/wax markers 1401, 1402, but comparable and all would be viable options for an X-ray maker.

A further R-shaped marker 1404 is pictured. This marker 1404 is made from gypsum cast with sodium. The amount of sodium used was between 1% and 12% by weight of the gypsum-sodium mixture, more particularly between 4% and 10%, and specifically around 7%, in the embodiment being described The gypsum/sodium marker is approximately 2 mm thick in the embodiment being described. The gypsum-sodium blend was found to expel more water during curing than the pure gypsum or gypsum/bronze markers discussed above, so resulting in a thinner marker than the other listed blends. The brightness/radiopacity is similar to that of the gypsum/bronze marker 1403.

Finally, a square piece of (dried but unfired) earthenware clay 1405 is pictured. The earthenware marker is approximately 2 mm thick, with varying brightness due to varying thickness (approximately 2.5 mm thick in the top right hand corner). The brightness/radiopacity is similar to that of the gypsum/bronze marker 1403.

The skilled person would appreciate that the radiopacity of all five material options 1401-1405 would be viable for use as an X-ray side marker at suitable thicknesses (e.g. between 2 and 5 mm, for example around 3 mm).

Further tests of ceramics, including unglazed earthenware and stoneware fired clays and glazed earthenware fired clays also demonstrated sufficient radio-opacity for use as X-ray markers with thicknesses between 2 and 5 mm. For the ceramics tested, very little difference in radio-opacity was detected between 2 mm thickness and 5 mm thickness.

In the method 1500 of an embodiment, as shown in FIG. 15, the wax (in this case, beeswax) was heated to its melting point, and kept at or above its melting point as mineral powder (e.g. gypsum powder) was added and mixed in. In the embodiment being described, the ratio of wax to mineral powder used was between 2:3 and 3:4 (wax:mineral).

This produced a material (a wax/mineral blend) that remained soft and malleable above 60° C.

In the embodiment being described, a mould 1510 is first heated 1501 to a temperature at which the material remains malleable (e.g. a temperature between 60° C. and 120° C., for example 65° C.).

In the embodiment being described, the mould 1510 is a silicone mould. The skilled person will appreciate that other materials may be used in other embodiments.

In the embodiment being described, the mould 1510 is rigid, and in particular is sufficiently rigid for a roller 1512 to be used as described below. In other embodiments, for example embodiments in which no roller is used and/or in which the mould is otherwise supported, a less rigid mould may be used.

The malleable material is then placed 1502 into the mould 1510.

In the embodiment being described, the mould 1510 has multiple indentations, each for use in making one side marker. In the embodiment being described, each indentation in the mould 1510 is R-shaped, such that the mould is intended for making right side markers. In alternative embodiments, the indentations may all be L-shaped, or may be shaped to provide a different side marker symbol. In alternative embodiments, the same mould may include both R-shaped and L-shaped indentations—i.e. one mould may be used to make both left and right side markers.

In the embodiment being described, an at least substantially equal amount of the material is placed 1502 into each indentation.

In the embodiment being described, a roller 1512 is then rolled 1503-1504 across the mould, pressing the wax/mineral blend flat. The skilled person will appreciate that the pressure may help to ensure that the shapes formed are similar/substantially identical, and/or that they take on the shape of the indentation clearly.

In alternative embodiments, a press may be used instead of a roller, and/or the mould 1510 may be heated to a high enough temperature that the material liquefies and adapts to the mould shape without pressure. Alternatively, rougher shapes may be accepted in some embodiments.

In the embodiment being described, the mould 1510 is then allowed to cool 1505 to a temperature at which the material sets; for example to below 60° C., optionally below 40° C., and further optionally below or equal to 25° C.

The letters formed are then removed 1506 from the mould 1510 once it has cooled.

The letters may be used as markers 100 as they are, or may be coated or encased in another material, providing a protective layer. Alternatively or additionally, the letters may be fired in some embodiments.

FIG. 16 illustrates an alternative method 1600 of making a side marker 100 which may be useable with a wide range of powdered materials (e.g. powdered minerals), even without casting and/or a binder.

At step 1601, a mould or shell 102 is provided. The mould 102 has a concave shaped region 104 arranged to receive a radiopaque substance 108 such as a powdered mineral. The concave shaped region 104 is arranged to cause the radiopaque substance 108 to take the shape of a symbol arranged to indicate one of a left or a right side such that the marker formed therefrom can be a side marker 100.

In the embodiment being described, the symbol is the letter "R", for use as a right side marker.

In the embodiment being described, the mould 102 is made from paper and/or starch pulp. In other embodiments, additional or alternative materials may be used. The skilled person will appreciate that cheap, environmentally-friendly, and/or bio-degradable materials may be selected for disposable markers 100. In some embodiments, for example embodiments in which the marker 100 is desired to be wipe-clean and/or waterproof, a polymeric material may be used.

At step 1602, the mould 102 is filled with a radio-opaque powder 108 (such as powdered eggshells). The powder is selected to be sufficiently fine-grained to take the shape of the mould 102.

At step 103, the mould is sealed with a backing sheet 106. In the embodiment being described, an adhesive laminate material is used for the backing sheet 106. In alternative or additional embodiments, an adhesive may be applied to the mould 102 and/or to the backing sheet 106 before the backing sheet 106 is attached to the mould 102.

The backing sheet 106 seals the radio-opaque powder 108 into the mould 102.

In the embodiment being described, the perimeter of the backing sheet 106 is the same as the perimeter of the mould 102 such that they are joined along their respective edges. In alternative embodiments, the backing sheet 106 may extend beyond the edges of the mould 102.

In the embodiment being described, the mould 102 provides a front face for the marker 100 and the backing sheet 106 provides a back face—i.e. the symbol is intended to be read with the front face 102 of the maker 100 towards the viewer. In the embodiment being described, the mould 102 is therefore turned 1604 through 180° after the backing sheet 106 is in place to provide a front view. In alternative embodiments, the backing sheet 106 may provide the front face and/or step 1604 may not be performed.

In some embodiments, the marker 100 may be complete following step 1603. However, in the embodiment being described, the filled mould 102 is mounted 1605 on a carrier sheet 110 to form the finished marker 100. In the embodiment being described, the carrier sheet 110 comprises two layers of paper or card, with a first layer having a hole therethrough arranged to receive the mould/backing sheet 102/106, the hole exposing a region of the second layer (beneath the first layer in the orientation shown).

In the embodiment being described, the mould/backing sheet 102/106 is inserted into the hole through the first layer such that the backing sheet 106 is adhered to the region of the second layer exposed by the hole through the first layer. The first layer therefore provides a lip around the R-shaped region 104. In the embodiment being described, the first layer is selected to be thicker than the backing sheet 106 such that the full depth of the backing sheet and a (in this embodiment, relatively small) portion of the depth of the mould 102 is received in the hole. In the embodiment being described, the hole is shaped and sized to engagingly receive the filled mould 102 and backing sheet 106.

The skilled person will appreciate that the carrier sheet 110 may serve to protect or shield the join between the backing sheet 106 and the mould 102, potentially reducing the risk of the backing sheet peeling or tearing away from the mould 102 and spilling the powder.

In alternative embodiments, the carrier sheet 110 may be adhered directly to the mould 102 in step 1603, taking the place of, and performing the role of, the backing sheet 106.

The finished marker 100 results, as shown in step 1606.

Unlike in the method 300 described above (in which the wet gypsum dries/cures to form the core 108), the core 108 of the marker 100 formed by the method 1600 being described is, and remains as, a powder rather than a single solid form. The skilled person would appreciate that a mould 102 or shell as described herein may be used to contain and protect a single solid form, or to contain, protect and maintain the shape of an amount of powder. As the powder used in the method 1600 being described is not sintered or fired to form a solid shape, nor mixed with a binder, it may be described as loose—it is only the mould 102 holding the loose powder in the desired shape.

The skilled person would appreciate that various different materials and combinations of materials may be used to make markers 100 as described, or similar to those described, above.

For example, any of the below ceramics or minerals, alone or in combination, may be used as a, or the, radio-opaque component of a marker 100:

Ceramics:
    Fired earthenware clay—unglazed
    Fried earthenware clay—glazed
    Fired stoneware clay—unglazed
    Fired stoneware clay—glazed
    Fired porcelain clay—unglazed
    Fired porcelain clay—glazed
    Glass Minerals:
    gypsum
    bentonite clay
    salt
    graphite
    bronze powder
    brass powder
    iron powder
    iron filings
    sodium bicarbonate
    egg shells (calcium carbonate)

Further, any one or more of the following polymers may be used as a binding, suspending or blending agent with any of the minerals above:
    beeswax
    soy wax
    paraffin wax
    acrylates
    polyesters
    polyurethanes
    silicones
    latex
    epoxies
    polylactic acid The skilled person will appreciate that a mould 102 (e.g. a moulded paper or starch form or polymer form) may be used to hold any of the minerals/ceramics listed above, either as a powder or in a solid form. The solid form or powder may be sealed inside the moulded shape, e.g. a moulded paper shape or polymer shape.

Further, in some embodiments a laminate of paper, wax and/or another polymer (e.g. a polymeric film or coating) may be used to hold one or more minerals or ceramics listed above, in either powder or a solid form sealed inside the laminate material. An adhesive laminate may be used to facilitate sealing. The adhesive laminate may form the whole of the protective form (e.g. the mould 103 and backing sheet 106) or may just be used as a backing sheet 106 on e.g. a polymeric or paper mould 102.

The skilled person will appreciate that, for the ceramics listed above, a covering such as the moulded paper or polymeric mould 102 and backing sheet 106 may not be provided. The ceramic may have sufficient structural integrity without a support/shell.

The skilled person will appreciate that wood may be used instead of, or as well as, the paper, starch polymeric or laminate materials mentioned above. For example, a hollow wooden profile could be filled with a radiopaque powder, e.g. one of the minerals listed above, and sealed. The wooden profile may be, for example, laser-cut, die-cut, CNC-cut or router cut from a flat sheet of wood, and may be sealed, for example, with one or more of paper, wood or a wax.

In embodiments in which the marker 100 is to be a disposable marker, a radio-sensitive material such as a radio-sensitive paper, film, and/or ink may be applied to, or used in the forming of, each marker 100.

The skilled person will appreciate that a radio-sensitive material will develop/react once exposed to X-rays, evidencing that the marker 100 has been used and should be disposed of. For example, the radio-sensitive material may change colour as a result of X-ray exposure.

The skilled person will appreciate that the embodiments described herein are provided by way of example only, and that the skilled person would be able to envisage other material combinations suitable for X-ray markers and other marker fabrication methods without departing from the scope of the invention as claimed.

The invention claimed is:

1. A disposable x-ray side marker comprising a non-metallic material having a sufficiently high linear attenuation coefficient to be radiographically visible, wherein the marker comprises a core at least partially surrounded by a sealing layer, wherein the sealing layer is arranged to act as a mould for casting of the core, and wherein the core is arranged to be retained within the mould.

2. The disposable x-ray side marker of claim 1, wherein the material is mouldable.

3. The disposable x-ray side marker of claim 1, wherein the material has an average atomic number greater than or equal to eleven.

4. The disposable x-ray side marker of claim 1, wherein the material has a linear attenuation coefficient greater than that of mammalian soft tissue.

5. The disposable x-ray side marker of claim 1, wherein gypsum is the main or only x-ray attenuating material of the marker.

6. The disposable x-ray side marker of claim 1, wherein a ceramic is the main or only x-ray attenuating material of the marker.

7. The disposable x-ray side marker of claim 1, wherein the sealing layer comprises a coating of a protective material on the core.

8. The disposable x-ray side marker of claim 1 wherein the core comprises a loose mineral powder.

9. The disposable x-ray side marker of claim 1 wherein the marker comprises no transition metals and/or heavy metals.

10. Use of a non-metallic material as an x-ray attenuating material in an x-ray side marker, wherein the x-ray side marker is the disposable x-ray side marker of claim 1.

11. The use of claim 10, wherein the non-metallic material is the main or only x-ray attenuating material in the x-ray side marker.

12. The use of claim 10, wherein the non-metallic material is gypsum, and wherein the gypsum is unfired.

13. The use of claim 10, wherein the use comprises:
marking a radiographic image of a subject, taken by an x-ray imaging apparatus, the marking comprising:
positioning at least one x-ray side marker near the subject and at least partially within a view area of the imaging apparatus;
recording the image whilst the x-ray side marker is in position.

14. A method of making a disposable x-ray side marker with no substantial metallic component, the method comprising:
forming a sealing layer out of a first material, the first material having a low linear attenuation coefficient, wherein the sealing layer acts as a mould;
at least partially filling the mould with a second material to form a core, the second material having a sufficiently high linear attenuation coefficient to be radiographically visible; and
covering the filled mould with the first material.

15. The method of claim 14, wherein the first material is paper and the second material is gypsum.

16. The method of claim 14 wherein the second material is gypsum, and wherein the method further comprises allowing the gypsum to cure rather than firing it.

* * * * *